(12) United States Patent
Lee et al.

(10) Patent No.: US 8,933,278 B2
(45) Date of Patent: Jan. 13, 2015

(54) PROCESS FOR PRODUCING ETHANOL AND REDUCING ACETIC ACID CONCENTRATION

(75) Inventors: David Lee, Seabrook, TX (US); Adam Orosco, Houston, TX (US); Claudio Ribeiro, Houston, TX (US); R. Jay Warner, Houston, TX (US); Robert Alan Deck, Richmond, TX (US); Emily Duff, League City, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 447 days.

(21) Appl. No.: 13/457,267

(22) Filed: Apr. 26, 2012

(65) Prior Publication Data

US 2012/0277496 A1 Nov. 1, 2012

Related U.S. Application Data

(63) Continuation-in-part of application No. 13/094,588, filed on Apr. 26, 2011, now Pat. No. 8,686,200, and a continuation-in-part of application No. 13/094,643, filed on Apr. 26, 2011, now Pat. No. 8,686,199, and a continuation-in-part of application No. 13/292,914, filed on Nov. 9, 2011.

(51) Int. Cl.
| | |
|---|---|
| *C07C 29/149* | (2006.01) |
| *C07C 29/80* | (2006.01) |
| *C07C 27/04* | (2006.01) |
| *C07C 51/12* | (2006.01) |
| *C07C 67/08* | (2006.01) |
| *C07C 67/54* | (2006.01) |

(52) U.S. Cl.
CPC ............. *C07C 51/12* (2013.01); *C07C 29/149* (2013.01); *C07C 29/80* (2013.01); *C07C 67/08* (2013.01); *C07C 67/54* (2013.01)
USPC ............................ 568/885; 568/913; 568/918

(58) Field of Classification Search
CPC ........ C07C 29/149; C07C 29/80; C07C 27/04
USPC .......................................... 568/885, 913, 918
See application file for complete search history.

(56) References Cited

U.S. PATENT DOCUMENTS

| | | | |
|---|---|---|---|
| 2,607,807 A | 8/1952 | Ford | |
| 2,649,407 A | 8/1953 | Harrison et al. | |
| 2,702,783 A | 2/1955 | Harrison et al. | |
| 2,801,209 A | 7/1957 | Muller et al. | |
| 2,882,244 A | 4/1959 | Milton | |
| 3,102,150 A | 8/1963 | Hunter et al. | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Karl et al. | |
| 3,769,329 A | 10/1973 | Paulik et al. | |
| 3,990,952 A | 11/1976 | Katzen et al. | |
| 4,126,539 A | 11/1978 | Derr, Jr. et al. | |
| 4,149,940 A | 4/1979 | Pinto | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulpranthipanja et al. | |
| 4,352,940 A | 10/1982 | Adelman et al. | |
| 4,379,028 A | 4/1983 | Berg et al. | |
| 4,395,576 A | 7/1983 | Kwantes et al. | |
| 4,398,039 A | 8/1983 | Pesa et al. | |
| 4,421,939 A | 12/1983 | Kiff et al. | |
| 4,422,903 A | 12/1983 | Messick et al. | |
| 4,443,639 A | 4/1984 | Pesa et al. | |
| 4,454,358 A | 6/1984 | Kummer et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,517,391 A | 5/1985 | Schuster et al. | |
| 4,520,213 A | 5/1985 | Victor | |
| 4,541,897 A | 9/1985 | Sommer et al. | |
| 4,615,806 A | 10/1986 | Hilton | |
| 4,626,321 A | 12/1986 | Grethlein et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,842,693 A | 6/1989 | Wheldon | |
| 4,886,905 A | 12/1989 | Larkins et al. | |
| 4,908,477 A | 3/1990 | Hartmann et al. | |

(Continued)

FOREIGN PATENT DOCUMENTS

| | | |
|---|---|---|
| CN | 201768393 | 3/2011 |
| CN | 102228831 | 11/2011 |

(Continued)

OTHER PUBLICATIONS

International Search Report and Written Opinion mailed Jul. 6, 2012 in corresponding international Application No. PCT/US2011/059889.
International Search Report and Written Opinion mailed Aug. 6, 2012 in corresponding International Application No. PCT/US2012/035196.
Anonymous, "Studies in Extractive and Azeotropic Distillation Series; Study No. 4—Separation of Alcohols from the Acetate/Alcohol/Water Ternary by Extractive Distillation", May 9, 2008, pp. 1-9, XP 55033135, Retrieved from the Internet: http://www.brix-berg.com/study4.htm pp. 1-4.
International Search Report and Written Opinion mailed Aug. 2, 2012 for International Application No. PCT/US2012/035220.
Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.
ZeaChem, Inc., Technology Overview, Lakewood, Colorado www.zeachem.com, 2008.

(Continued)

*Primary Examiner* — Elvis O Price

(57) ABSTRACT

A process for producing ethanol and, in particular, to a process for reducing the concentration of acetic acid in a crude ethanol product by esterifying unreacted acetic acid with an alcohol.

20 Claims, 4 Drawing Sheets

(56) References Cited

U.S. PATENT DOCUMENTS

| | | | |
|---|---|---|---|
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg |
| 5,124,004 A | 6/1992 | Grethlein et al. |
| 5,139,981 A | 8/1992 | Kurland |
| 5,144,068 A | 9/1992 | Smith et al. |
| 5,149,680 A | 9/1992 | Kitson et al. |
| 5,185,481 A | 2/1993 | Muto et al. |
| 5,198,592 A | 3/1993 | Van Beijnum et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,414,161 A | 5/1995 | Uhm et al. |
| 5,415,741 A | 5/1995 | Berg |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,502,248 A | 3/1996 | Funk et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Gaddy et al. |
| 5,861,530 A | 1/1999 | Atkins et al. |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,223,886 B2 | 5/2007 | Scates et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,588,690 B1 | 9/2009 | Tsao |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,718,039 B2 | 5/2010 | Dirkzwager et al. |
| 7,732,173 B2 | 6/2010 | Mairal et al. |
| 7,744,727 B2 | 6/2010 | Blum et al. |
| 7,834,223 B2 | 11/2010 | Atkins et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 2003/0013908 A1 | 1/2003 | Horan et al. |
| 2003/0077771 A1 | 4/2003 | Verser et al. |
| 2006/0019360 A1 | 1/2006 | Verser et al. |
| 2006/0106246 A1 | 5/2006 | Warner et al. |
| 2006/0127999 A1 | 6/2006 | Verser et al. |
| 2007/0031954 A1 | 2/2007 | Mairal et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0221725 A1 | 9/2009 | Chorney et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0130775 A1 | 5/2010 | Voss et al. |
| 2010/0137630 A1 | 6/2010 | Garton et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0185628 A1 | 8/2011 | Johnston et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |
| 2012/0010437 A1 | 1/2012 | Jevtic |
| 2012/0010438 A1 | 1/2012 | Lee et al. |
| 2012/0010445 A1 | 1/2012 | Johnston et al. |
| 2012/0277481 A1 | 11/2012 | Warner |
| 2012/0323049 A1 | 12/2012 | Lee |
| 2012/0323050 A1 | 12/2012 | Lee |

FOREIGN PATENT DOCUMENTS

| | | |
|---|---|---|
| CN | 102229520 | 11/2011 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |

(56) References Cited

FOREIGN PATENT DOCUMENTS

| | | |
|---|---|---|
| EP | 0372847 | 6/1990 |
| EP | 0456647 | 11/1991 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| JP | 6-116182 | 4/1994 |
| JP | 2001-046874 | 2/2001 |
| WO | WO 83/03409 | 10/1983 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |
| WO | WO 2011/053365 | 5/2011 |
| WO | WO 2011/097193 | 8/2011 |
| WO | WO 2011/097219 | 8/2011 |
| WO | WO 2011/097220 A2 | 8/2011 |
| WO | WO 2011/097227 A2 | 8/2011 |
| WO | WO 2012/006219 A2 | 1/2012 |
| WO | WO 2012/006228 | 1/2012 |
| WO | WO 2012/006499 | 1/2012 |

OTHER PUBLICATIONS

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

J. Jones, "The Cativa™ Process for the Manufacture of Acetic Acid", Platinum Metals Review, vol. 44, No. 36, pp. 94-104 (Jul. 2000).

International Search Report and Written Opinion mailed Jun. 29, 2012 in corresponding International Application No. PCT/US2011/060014.

H. Constantin et al., "Influence of C-Sources on the Denitrification Rate of a High-Nitrate Concentrated Industrial Wastewater", Wat. Res., 1997, vol. 31, No. 3, pp. 583-589.

International Search Report and Written Opinion mailed May 29, 2012 in corresponding International Application No. PCT/US2011/059887.

V. Ragaini et al., "Increasing the value of dilute acetic acid streams through esterification Part I. Experimental analysis of the reaction zone", Applied Catalysis B: Environmental, 64, 2006, pp. 66-71.

Z. P. Xu et al., "Kinetics of Acetic Acid Esterification over Ion Exchange Catalysts", Journal of Chemical Engineering, Aug. 1996, vol. 74, pp. 493-500.

Witzeman and Agreda in "Acetic Acid and its Derivatives,", Marcel Dekker, NY, 1992, p. 271.

International Search Report and Written Opinion mailed Sep. 2, 2011 in corresponding International Application No. PCT/US2011/023276.

Written Opinion mailed May 8, 2012 in corresponding International Application No. PCT/US2011/023276.

International Search Report and Written Opinion mailed Jul. 11, 2012 in corresponding International Application No. PCT/US2012/035203.

International Search Report and Written Opinion for PCT/US2012/035189 mailed Jul. 30, 2012.

International Search Report and Written Opinion for PCT/US2012/035273 mailed Jul. 30, 2012.

Simo, et al., "Adsorption/Desorption of Water and Ethanol on 3A Zeolite in Near-Adiabatic Fixed Bed," Industrial & Engineering Chemistry Research, vol. 48, No. 20, Sep. 2009, XP55027304, pp. 9247-9260.

Benson, et al., "Cellulose Based Adsorbent Materials for the Dehydration of Ethanol Using Thermal Swing Adsorption," Adsorption, Kluwer Academic Publishers, vol. 11, No. 1, Jul. 2005, XP019203738, pp. 697-701.

Huang, et al., "Low-Energy Distillation-Membrane Separation Process," Industrial & Engineering Chemistry Research, American Chemical Society, vol. 49, No. 8, Jan. 2010, XP002657719, pp. 3760-3768.

Response to Final Office Action for U.S. Appl. No. 13/094,488, filed Oct. 18, 2013.

Response to Final Office Action for U.S. Appl. No. 13/094,661, filed Nov. 25, 2013.

Response to Final Office Action for U.S. Appl. No. 13/162,005, filed Nov. 26, 2013.

Response to Final Office Action for U.S. Appl. No. 13/162,034 filed, Nov. 27, 2013.

H. Kita et al., "Synthesis of a Zeolite NAA Membrane for Pervaporation of Water/Organic Liquid Mixtures", Journal of Materials Science Letters, vol. 14, Jan. 1, 1995, XP 001194463, pp. 206-208.

Kaj Jakobsson et al., "Modeling of a side reactor configuration combining reaction and distillation", Chemical Engineering Science, vol. 57, 2002, pp. 1521-1524.

International Search Report and Written Opinion mailed Nov. 12, 2012 in corresponding International Application No. PCT/US2012/035271.

International Preliminary Report on Patentability for PCT/US2012/035271 mailed Nov. 7, 2013.

US 8,933,278 B2

PROCESS FOR PRODUCING ETHANOL AND REDUCING ACETIC ACID CONCENTRATION

CROSS REFERENCE TO RELATED APPLICATION

This application is a continuation-in-part of U.S. application Ser. No. 13/094,588, filed on Apr. 26, 2011, U.S. application Ser. No. 13/094,643, filed on Apr. 26, 2011, and U.S. application Ser. No. 13/292,914, filed on Nov. 9, 2011, the entire contents and disclosures of which are incorporated herein by reference.

FIELD OF THE INVENTION

The present invention relates generally to processes for producing alcohol and, in particular, to a process for reducing the concentration of acetic acid in a crude ethanol product.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulosic materials, such as corn or sugar cane. Conventional methods for producing ethanol from organic feed stocks, as well as from cellulosic materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 7,842,844 describes a process for improving selectivity and catalyst activity and operating life for the conversion of hydrocarbons to ethanol and optionally acetic acid in the presence of a particulate catalyst, said conversion proceeding via a syngas generation intermediate step.

In addition, when conversion is incomplete, unreacted acid remains in the crude ethanol product, which must be removed to recover ethanol. Other processes, such as those described in U.S. Pat. No. 5,599,976, involve a process for treating aqueous streams comprising up to 50 wt. % acetic acid in a catalytic distillation unit to react the acetic acid with methanol to form recyclable methyl acetate and water.

The need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising hydrogenating acetic acid and/or an ester thereof in a reactor in the presence of a catalyst to form a crude ethanol product, separating a portion of the crude ethanol product in a first distillation column to yield a first distillate comprising acetaldehyde and ethyl acetate, and a first residue comprising ethanol, acetic acid, and water, and separating a portion of the first residue in a second distillation column to yield a second residue comprising acetic acid, e.g., from 90% to 99.9% of the acetic acid in the crude ethanol product, and water and a second distillate comprising ethanol. The acetic acid from a first portion of the second residue is reacted with at least one alcohol in an esterification unit to produce at least one ester product stream, and a water stream that is substantially free of acetic acid, e.g., preferably less than 1 wt. % acetic acid. The alcohol is selected from the group consisting of methanol, ethanol, propanol, butanol, pentanol, and isomers and mixtures thereof. The process also involves recovering ethanol from the second distillate. In one embodiment, the first residue and the second distillate comprise ethyl acetate, and further comprising separating the second distillate in a third distillation column to yield a third distillate comprising ethyl acetate and third residue comprising ethanol. In some embodiments, the second distillate may also comprise water, and further comprising removing the water prior to the third column.

In a second embodiment, the present invention is directed to a process for producing ethanol, comprising hydrogenating acetic acid and/or an ester thereof in a reactor in the presence of a catalyst to form a crude ethanol product, separating a portion of the crude ethanol product in a first distillation column to yield a first distillate comprising acetaldehyde and ethyl acetate, and a first residue comprising ethanol, acetic acid, and water, separating a portion of the first residue in a second distillation column to yield a second residue comprising acetic acid and water and a second distillate comprising ethanol, reacting the acetic acid from a first portion of the second residue with methanol in an esterification unit to produce at least one ester product stream comprising methanol, methyl acetate, and a water stream, provided that the at least one ester product stream and water stream are substantially free of acetic acid, and recovering ethanol from the second distillate.

In a third embodiment, the present invention is directed to a process for producing ethanol, comprising hydrogenating acetic acid and/or an ester thereof in a reactor in the presence of a catalyst to form a crude ethanol product, separating a portion of the crude ethanol product in a first distillation column to yield a first distillate comprising acetaldehyde and ethyl acetate, and a first residue comprising ethanol, acetic acid, and water, separating a portion of the first residue in a second distillation column to yield a second residue comprising acetic acid and water and a second distillate comprising ethanol and ethyl acetate, reacting the acetic acid from a first portion of the second residue with at least one alcohol in an esterification unit to produce at least one ester product stream, and a water stream that is substantially free of acetic acid, and separating a portion of the second distillate in a third distillation column to yield a third distillate comprising ethyl acetate and third residue comprising ethanol. In some embodiments, the second distillate may also comprise water, and further comprising removing the water prior to the third column.

In a fourth embodiment, the present invention is directed to process for integrated a hydrogenation process and carbonylation process. The integrated process comprises hydrogenating acetic acid and/or an ester thereof in a hydrogenation reactor in the presence of a catalyst to form a crude ethanol product, separating a portion of the crude ethanol product in a first distillation column to yield a first distillate comprising acetaldehyde and ethyl acetate, and a first residue comprising ethanol, acetic acid, and water, separating a portion of the first residue in a second distillation column to yield a second residue comprising acetic acid and water and a second distillate comprising ethanol and ethyl acetate, and reacting the acetic acid from a first portion of the second residue with at least one alcohol, preferably methanol, in an esterification unit to produce at least one ester product stream that comprises methyl acetate, and a water stream. The ester product stream is reacted with carbon monoxide, under carbonylation conditions, to form acetic acid and the resulting acetic acid is directed to the hydrogenation reactor. In one embodiment, the resulting acetic acid is substantially free of methanol and methyl acetate. The integrated process also involves recovering ethanol from the second distillate.

In a fifth embodiment, the present invention is directed to a process for producing ethanol, comprising hydrogenating acetic acid and/or an ester thereof in a reactor in the presence of a catalyst to form a crude ethanol product, separating a portion of the crude ethanol product in a first distillation column that is an extractive column to yield a first distillate comprising acetaldehyde and ethyl acetate, and a first residue comprising ethanol, acetic acid, and water, and separating a portion of the first residue in a second distillation column to yield a second residue comprising acetic acid and water and a second distillate comprising ethanol. The acetic acid from a first portion of the second residue is reacted with at least one alcohol in an esterification unit to produce at least one ester product stream, and a water stream. The extractive agent fed to the first distillation column, preferably above the fed point of the crude ethanol product, may be obtained from a second portion of the second residue and/or from the water stream. The process also involves recovering ethanol from the second distillate.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
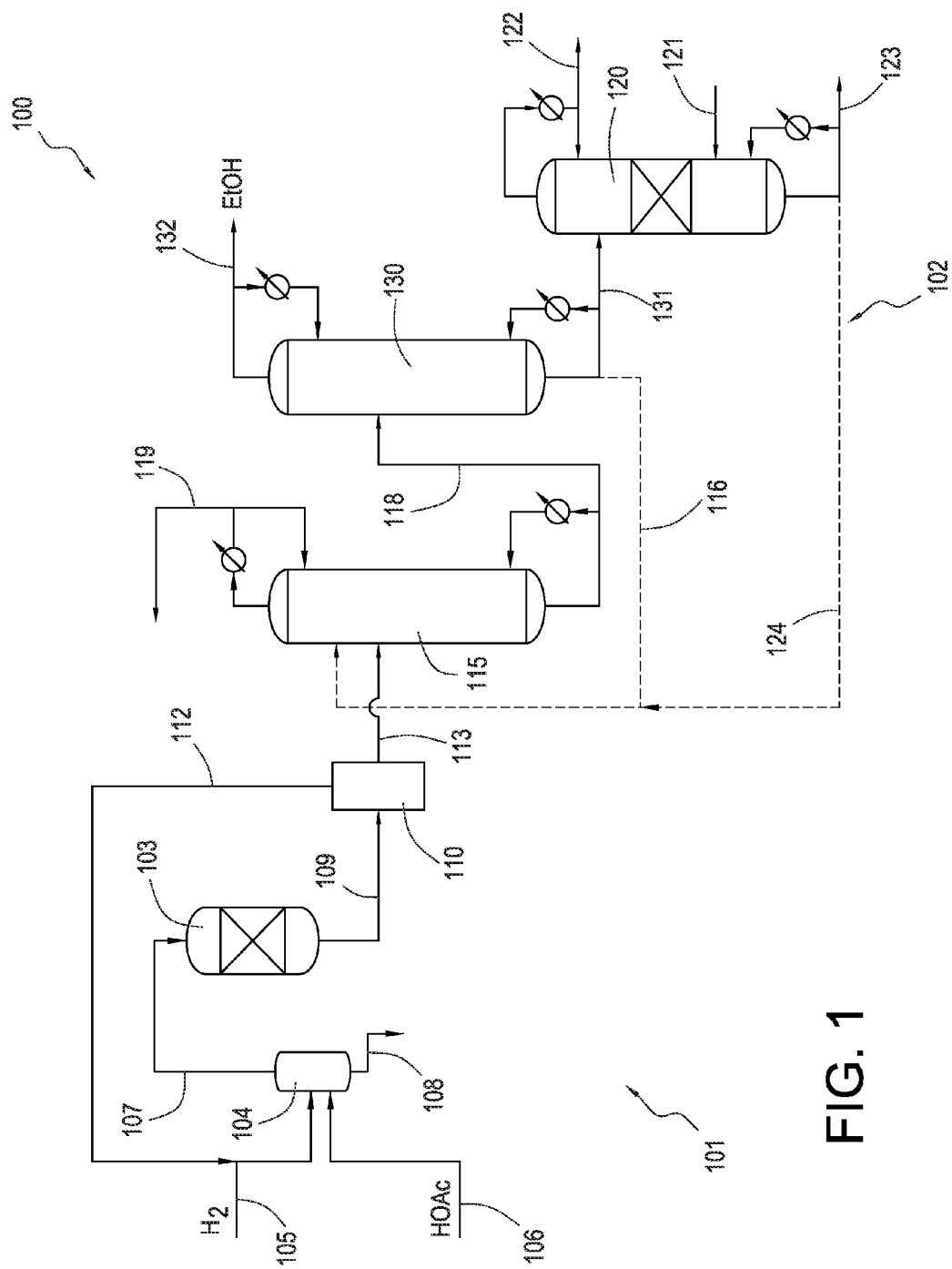
FIG. 1 is a schematic diagram of an acetic acid reduction system for an ethanol production process in accordance with one embodiment of the present invention.

The present invention relates to processes for recovering alcohols, in particular ethanol produced by hydrogenating acetic acid in the presence of a catalyst. The hydrogenation reaction produces a crude ethanol product that comprises ethanol, water, ethyl acetate, unreacted acetic acid, and other impurities. To improve operating efficiencies, the processes of the present invention involve separating the crude ethanol product into a dilute acid stream comprising water and unreacted acetic acid and an ethanol product stream. While it may be possible to separate acetic acid from the dilute acid stream, it may be more beneficial to react the acetic acid with one or more alcohols to form one or more ester products. The resulting ester product(s) beneficially may be easier to separate from the water, resulting in an overall improved separation process.

In some embodiments, the ester product(s) may be further processed and/or refined, and then recycled to the reaction process or to another reaction process such as an acetic acid production facility, an esters plant, or a hydrogenolysis unit. When integrated with an acetic acid production facility the acetic acid may be fed back to the hydrogenation reaction, as described in U.S. application Ser. No. 13,094,661, filed on Apr. 26, 2011, the entire contents and disclosures of which are hereby incorporated by reference. The ester product stream preferably comprises methyl acetate and methanol is reacted with carbon monoxide, under carbonylation conditions, to form acetic acid and the resulting acetic acid is directed to the hydrogenation reactor. In one embodiment, the resulting acetic acid is substantially free of methanol and methyl acetate.

Recovery of acetic acid from the dilute acid stream through an ester intermediate according to the processes of the present invention may be desirable when the dilute acid stream comprises from 0.5 to 60 wt. % acetic acid, e.g., from 1 to 50 wt. % acetic acid or from 2 to 20 wt. % acetic acid. At lower concentrations, it may be preferred to neutralize and dispose of the dilute acid stream in a waste water treatment system. At greater concentrations, it may be preferred to recycle the acetic acid to the reaction process, optionally after removing some or all of the water therefrom.

In one embodiment, substantially all of the unreacted acetic acid is recovered in the dilute acid stream. By removing substantially all of the unreacted acetic acid from the crude ethanol product, the process, in some aspects, advantageously does not require further separation of acetic acid from the ethanol product stream. In this aspect, the ethanol product stream may contain very low acetic acid concentrations, preferably in an amount less than 0.2 wt. %, less than 0.1 wt. % or less than 0.05 wt. %, and preferably only a trace amounts of acetic acid, such as an amount less than 100 wppm, less than 75 wppm or less than 50 wppm.

In some embodiments, the dilute acid stream is substantially free of ethanol or ethyl acetate. In this aspect, for example, the dilute acid stream may comprise less than 1 wt. % ethanol or ethyl acetate, collectively, e.g., less than 0.005 wt. %.

According to embodiments of the present invention, the acetic acid present in the dilute acid stream is reacted with an alcohol stream, e.g., methanol and/or ethanol, in an esterification unit to produce at least one ester and water, and separating the at least one ester from the water to produce an ester product stream comprising the at least one ester and a residue stream comprising water.

An esterification unit of the present invention comprises a reaction zone and a separation zone. In some embodiments, an esterification unit comprises a reactor coupled to one or more distillation columns. In other embodiments, the esterification unit comprises a reactive distillation column comprising a reaction section and a distillation section, to produce a distillate stream comprising at least one ester and a residue stream comprising water.

As indicated above, acetic acid from the dilute acid stream is reacted with one or more alcohols to form at least one ester. In some embodiments, the alcohol fed to the esterification unit is selected from the group consisting of methanol, ethanol, propanol, butanol, pentanol, and isomers and mixtures thereof. The alcohol is preferably fed to the esterification unit in a counter-current flow to the dilute acid stream to facilitate the production of the ester product(s). In some embodiments, the resulting ester is selected from the group consisting of methyl acetate, ethyl acetate, propyl acetate, butyl acetate, pentyl acetate, and isomers and mixtures thereof. The one or more esters produced by the process preferably correspond to the one or more alcohols that are fed to the esterification unit. For example, when methanol is fed to the esterfication unit, the methanol is reacted with acetic acid in the dilute acid stream to produce methyl acetate. In another embodiment, ethanol is reacted with acetic acid in the dilute acid stream to produce ethyl acetate.

The process parameters for the esterification step may vary widely depending, for example, on the catalyst employed and the ester being formed. In one embodiment, the esterification unit operates a base temperature from 100° C. to 150° C., e.g., from 100° C. to 130° C., or from 100° C. to 120° C. In terms of pressure, the esterification unit may be operated at atmospheric pressure, subatmospheric pressure, or superatmospheric pressure. For example, in some embodiments, the reactive distillation column operates at a pressure from 50 kPa to 500 kPa, e.g., from 50 kPa to 400 kPa, or from 50 kPa to 200 kPa.

The feed rate of the dilute acid stream to the esterification unit may be adjusted based on the molar ratio of acetic acid to alcohol being fed to the esterification unit. For example, in some embodiments, the molar ratio of acetic acid to methanol fed to the esterification unit is from 1:1 to 1:50, e.g., from 1:2 to 1:35, or from 1:5 to 1:20.

In some embodiments, the process further comprises reducing the at least one ester in the ester product stream to provide an alcohol product stream. A portion of the alcohol product stream may then be recycled to the crude ethanol product, reacted with the acetic acid from the dilute acid stream, or a combination thereof.

By removing a relatively large portion of the acetic acid from the crude ethanol product, in one embodiment, the process beneficially reduces the energy required for additional acetic acid removal steps since less acetic acid will be contained in the ethanol-containing distillate of the first column. In addition, acetic acid does not have to be recycled to the reactor.

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{12}C$ ratio of the methanol, acetic acid and/or ethanol may be from one half to about 1 of the $^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180, and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a syngas including hydrogen and carbon monoxide, are incorporated herein by reference in their entireties.

Acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system so that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The reactor pressure may range from 100 kPa to 4500 kPa, e.g., from 150 kPa to 3500 kPa, or from 500 kPa to 3000 kPa. The reactants may be fed to the reactor at a gas hourly space velocity (GHSV) from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds.

The hydrogenation of acetic acid to form ethanol is preferably conducted in the presence of a hydrogenation catalyst. Exemplary catalysts are further described in U.S. Pat. Nos. 7,608,744 and 7,863,489, and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments the catalyst may be a bulk catalyst.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %.

Preferred metal combinations for exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, or ruthenium/iron.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 20 wt. %, e.g., from 0.1 to 10 wt. %, or from 0.1 to 7.5 wt. %. In one embodiment, the catalyst may comprise platinum, tin and cobalt.

In addition to one or more metals, in some embodiments of the present invention the catalysts further comprise a support or a modified support. As used herein, the term "modified support" refers to a support that includes a support material and a support modifier, which adjusts the acidity of the support material. The total weight of the support or modified support, based on the total weight of the catalyst, preferably is from 75 to 99.9 wt. %, e.g., from 78 to 99 wt. %, or from 80 to 97.5 wt. %. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The support may be a modified support and the support modifier is present in an amount from 0.1 to 50 wt. %, e.g., from 0.2 to 25 wt. %, from 1 to 20 wt. %, or from 3 to 15 wt. %, based on the total weight of the catalyst. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. Preferred support modifiers include oxides of tungsten, molybdenum, and vanadium.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. The basic support modifier may be selected from the group consisting of oxides and metasilicates of any of sodium, potassium, magnesium, calcium, scandium, yttrium, and zinc, as well as mixtures of any of the foregoing. In one embodiment, the basic support modifier is a calcium silicate, such as calcium metasilicate ($CaSiO_3$). The calcium metasilicate may be crystalline or amorphous.

Catalysts on a modified support may include one or more metals from the group of platinum, palladium, cobalt, tin, or rhenium on a silica support modified by one or more modifiers from the group of calcium metasilicate, and oxides of tungsten, molybdenum, and vanadium.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

After the washing, drying and calcining of the catalyst is completed, the catalyst may be reduced in order to activate the catalyst. Reduction is carried out in the presence of a reducing gas, preferably hydrogen. The reducing gas is continuously passed over the catalyst at an initial ambient temperature that is increased up to 400° C. In one embodiment, the reduction is preferably carried out after the catalyst has been loaded into the reaction vessel where the hydrogenation will be carried out.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments a low conversion may be acceptable at high selectivity for ethanol.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. The productivity may range from 100 to 3,000 grams of ethanol per kilogram of catalyst per hour.

In various embodiments of the present invention, the crude ethanol product produced by the hydrogenation process, before any subsequent processing, such as purification and separation, will typically comprise acetic acid, ethanol and water. Exemplary compositional ranges for the crude ethanol product are provided in Table 1, excluding hydrogen. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product of Table 1 may have low concentrations of acetic acid with higher conversion, and the acetic acid concentration may range from 0.01 wt. % to 20 wt. %, e.g., 0.05 wt. % to 15 wt. %, from 0.1 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Exemplary ethanol recovery systems having esterification units in accordance with embodiments of the present invention are shown in FIGS. 1-4. According to FIG. 1, hydrogenation system 100 provides a suitable hydrogenation reactor and a process for separating acetic acid from a crude ethanol product. System 100 comprises reaction zone 101 and separation zone 102, which further comprises an esterification unit 120.

As shown in FIGS. 1-4, the feed to reactor 103 comprises fresh acetic acid. Hydrogen and acetic acid are fed to vaporizer 104 via lines 105 and 106, respectively, to create a vapor feed stream in line 107 that is directed to reactor 103. In one embodiment, lines 105 and 106 may be combined and jointly fed to the vaporizer 104. The temperature of the vapor feed stream in line 107 is preferably from 100° C. to 350° C., e.g., from 120° C. to 310° C. or from 150° C. to 300° C. Any feed that is not vaporized is removed from vaporizer 104, via blowdown 108. In addition, although line 107 is shown as being directed to the top of reactor 103, line 107 may be directed to the side, upper portion, or bottom of reactor 103.

Reactor 103 contains the catalyst that is used in the hydrogenation of the carboxylic acid, preferably acetic acid. In one embodiment, one or more guard beds (not shown) may be used upstream of the reactor, optionally upstream of vaporizer 104, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 103 via line 109.

The crude ethanol product may be condensed and fed to a separator 110, which, in turn, forms a vapor stream 112 and a liquid stream 113. In some embodiments, separator 110 may comprise a flasher or a knockout pot. Separator 110 may operate at a temperature from 20° C. to 350° C., e.g., from 30° C. to 325° C. or from 60° C. to 250° C. The pressure of separator 110 may be from 100 kPa to 3000 kPa, e.g., from 125 kPa to 2500 kPa or from 150 kPa to 2200 kPa. Optionally, the crude ethanol product in line 109 may pass through one or more membranes to separate hydrogen and/or other non-condensable gases.

Vapor stream 112 exiting separator 110 may comprise hydrogen and hydrocarbons, and may be purged and/or returned to reaction zone 101. As shown, vapor stream 112 is combined with the hydrogen feed 105 and co-fed to vaporizer 104. In some embodiments, the returned vapor stream 112 may be compressed before being combined with hydrogen feed 105.

Liquid stream 113 from separator 110 is withdrawn and directed as a feed composition to the side of first distillation column 115, also referred to as a "light ends column." Liquid stream 113 may be heated from ambient temperature to a temperature of up to 70° C., e.g., up to 50° C., or up to 40° C. The additional energy required to pre-heat liquid stream 113 above 70° C. does not achieve the desired energy efficiency in first column 115 with respect to reboiler duties.

In another embodiment, liquid stream 113 is not separately preheated, but is withdrawn from separator 110, and cooled if needed, at a temperature of less than 70° C., e.g., less than 50° C., or less than 40° C., and directly fed to first column 115.

In one embodiment, the contents of liquid stream 113 are substantially similar to the crude ethanol product obtained from the reactor, except that the composition has been depleted of hydrogen, carbon dioxide, methane or ethane, which have been removed by separator 110. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

FEED COMPOSITION TO COLUMN 115
(Liquid Stream 113)

| | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 5 to 80 | 0 to 35 |
| Water | 5 to 40 | 5 to 30 | 10 to 26 |
| Ethyl Acetate | <30 | 1 to 25 | 3 to 20 |
| Acetaldehyde | <10 | 0.001 to 3 | 0.1 to 3 |
| Acetal | <5 | 0.01 to 5 | 0.01 to 3 |
| Acetone | <5 | 0.0005 to 0.05 | 0.001 to 0.03 |

The amounts indicated as less than (<) in the tables throughout the present specification are preferably not present and if present may be present in amounts greater than 0.0001 wt. %.

In one embodiment, the ethyl acetate concentration in the liquid stream 113 may affect the first column reboiler duty and size. Decreasing ethyl acetate concentrations may allow for reduced reboiler duty and size. In one embodiment, to reduce the ethyl acetate concentration (a) the catalyst in reactor may convert ethyl acetate in addition to acetic acid; (b) the catalyst may be less selective for ethyl acetate, and/or (c) the feed to reactor, including recycles, may contain less ethyl acetate.

Figure 3:
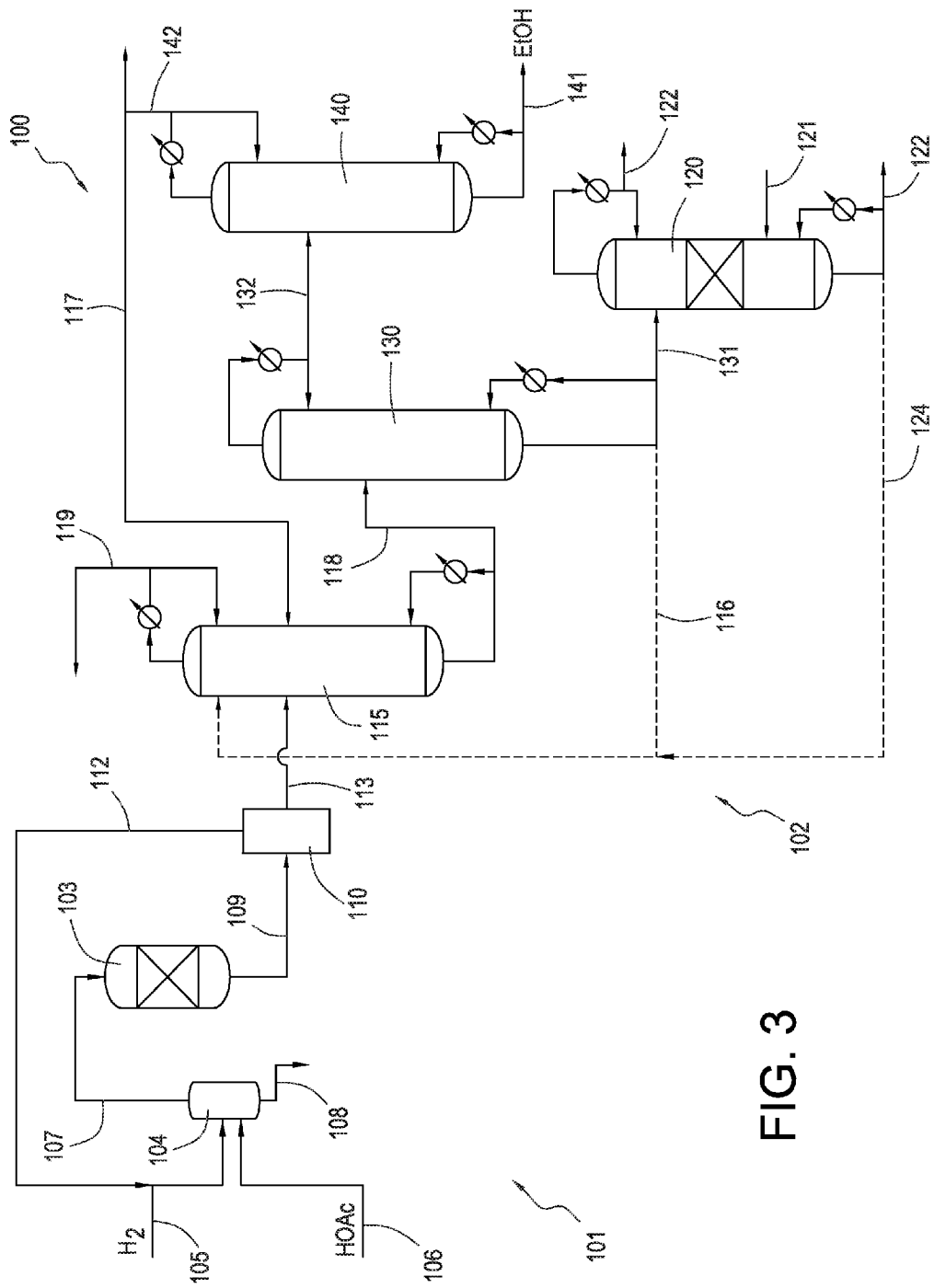
FIG. 3 is a schematic diagram of an acetic acid reduction system for an ethanol production process having a product column in accordance with one embodiment of the present invention.

In the embodiment shown in FIG. 1, liquid stream 113 is introduced in the upper part of first column 115, e.g., upper half or upper third. An ethyl acetate recycle stream 117 may also be fed to first column as shown in FIG. 3.

In one optional embodiment, an optional extractive agent 116 may also be used and is preferably introduced above liquid stream 113. Optional extractive agent 116 may be heated from ambient temperature to a temperature of up to 70° C., e.g., up to 50° C., or up to 40° C. In another embodiment, optional extractive agent 116 is not separately preheated, but is withdrawn from second column 130, and cooled, if necessary, to a temperature of less than 70° C., e.g., less than 50° C., or less than 40° C., and directly fed to first column 115.

Optional extractive agent 116 preferably comprises water that has been retained within the system. As described herein, optional extractive agent 116 may be obtained from a portion of the second residue. Optional extractive agent 116 may be a dilute acid stream comprising up to 20 wt. % acetic acid, e.g., up to 10 wt. % acetic acid or up to 5 wt. % acetic acid. In one embodiment, the mass flow ratio of water in extractive agent 116 to the mass flow of the organic feed, which comprises liquid stream 113 and ethyl acetate recycle stream 117, may range from 0.05:1 to 2:1, e.g., from 0.07 to 0.9:1 or from 0.1:1 to 0.7:1. It is preferred that the mass flow of extractive agent 116 is less than the mass flow of the organic feed.

In one embodiment, first column 115 is a tray column having from 5 to 90 theoretical trays, e.g. from 10 to 60 theoretical trays or from 15 to 50 theoretical trays. The number of actual trays for each column may vary depending on the tray efficiency, which is typically from 0.5 to 0.7 depending on the type of tray. The trays may be sieve trays, fixed valve trays, movable valve trays, or any other suitable design known in the art. In other embodiments, a packed column having structured packing or random packing may be employed.

When first column 115 is operated under 50 kPa, the temperature of the residue exiting in line 118 preferably is from 20° C. to 100° C., e.g., from 30° C. to 90° C. or from 40° C. to 80° C. The base of column 115 may be maintained at a relatively low temperature by withdrawing a residue stream comprising ethanol, ethyl acetate, water, and acetic acid, thereby providing an energy efficiency advantage. The temperature of the distillate exiting in line 119 from column 115 preferably at 50 kPa is from 10° C. to 80° C., e.g., from 20° C. to 70° C. or from 30° C. to 60° C. The pressure of first column 115 may range from 0.1 kPa to 510 kPa, e.g., from 1 kPa to 475 kPa or from 1 kPa to 375 kPa. In some embodiments, first column 115 may operate under a vacuum of less than 70 kPa, e.g., less than 50 kPa, or less than 20 kPa. Operating under a vacuum may decrease the reboiler duty and reflux ratio of first column 115. However, a decrease in operating pressure for first column 115 does not substantially affect column diameter.

In first column 115, a weight majority of the ethanol, water, acetic acid, are removed from the organic feed, including liquid stream 113 and ethyl acetate recycle stream 117, and are withdrawn, preferably continuously, as residue in line 118. This includes any water added as an optional extractive agent 116. Concentrating the ethanol in the residue reduces the amount of ethanol that is recycled to reactor 103 and in turn reduces the size of reactor 103. Preferably less than 10% of the ethanol from the organic feed, e.g., less than 5% or less than 1% of the ethanol, is returned to reactor 103 from first column 115. In addition, concentrating the ethanol also will concentrate the water and/or acetic acid in the residue. In one embodiment, at least 90% of the ethanol from the organic feed is withdrawn in the residue, and more preferably at least 95%. In addition, ethyl acetate may also be present in the first residue in line 118. The reboiler duty may decrease with an ethyl acetate concentration increase in the first residue in line 118.

First column 115 also forms an distillate in line 119 that may be condensed and refluxed, for example, at a ratio from 30:1 to 1:30, e.g., from 10:1 to 1:10 or from 5:1 to 1:5. Optionally, higher mass flow ratios of water, as an optional extractant, to organic feed may allow first column 115 to operate with a reduced reflux ratio.

First distillate in line 119 preferably comprises a weight majority of the acetaldehyde and ethyl acetate from liquid stream 113, as well as from ethyl acetate recycle stream 117. In one embodiment, the first distillate in line 119 comprises a concentration of ethyl acetate that is less than the ethyl acetate concentration for the azeotrope of ethyl acetate and water, and more preferably less than 75 wt. %.

In some embodiments, first distillate in stream 119 also comprises ethanol. Returning the ethanol may require an increase in reactor capacity to maintain the same level of ethanol efficiency. A separate extraction column and extractant may be used to recover ethanol from the first distillate in line 119 in some embodiments.

Exemplary components of the distillate and residue compositions for first column 115 are provided in Table 3 below. It should also be understood that the distillate and residue may also contain other components, not listed in Table 3. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

LIGHT ENDS COLUMN

|  | Conc. (wt. %) | Conc. (wt. %) | Conc. (wt. %) |
| --- | --- | --- | --- |
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Acetal | <3 | 0.01 to 2 | 0.05 to 1.5 |
| Acetone | <0.05 | 0.001 to 0.03 | 0.01 to 0.025 |
| Ethanol | <25 | 0.001 to 20 | 0.01 to 15 |
| Water | 0.1 to 20 | 1 to 15 | 2 to 10 |
| Acetic Acid | <2 | <0.1 | <0.05 |
| Residue |  |  |  |
| Acetic Acid | 0.1 to 50 | 0.5 to 40 | 1 to 30 |
| Water | 20 to 85 | 25 to 80 | 30 to 75 |
| Ethanol | 10 to 75 | 15 to 70 | 20 to 65 |
| Ethyl Acetate | 0.005 to 30 | 0.03 to 25 | 0.08 to 1 |

In one embodiment of the present invention, first column 115 may be operated at a temperature where most of the water, ethanol, and acetic acid are removed into the residue stream and only a small amount of ethanol and water is collected in the distillate stream due to the formation of binary and tertiary azeotropes. The weight ratio of water in the residue in line 118 to water in the distillate in line 119 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 103. In one embodiment, when the conversion in the hydrogenation reactor is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The first distillate in line 119 preferably is substantially free of acetic acid, e.g., comprising less than 1000 wppm, less than 500 wppm or less than 100 wppm acetic acid. The distillate may be purged from the system or recycled in whole or part to reactor 103. In some embodiments, when the distillate comprises ethyl acetate and acetaldehyde, the distillate may be further separated, e.g., in a distillation column (not shown), into an acetaldehyde stream and an ethyl acetate stream. The ethyl acetate stream may also be hydrolyzed or reduced with hydrogen, via hydrogenolysis, to produce ethanol. Either of these streams may be returned to reactor 103 or separated from system 100 as additional products.

Some species, such as acetals, may decompose in first column 115 so that very low amounts, or even no detectable amounts, of acetals remain in the distillate or residue.

To recover ethanol, first residue in line 118 may be further separated depending on the concentration of acetic acid and/or ethyl acetate. In most embodiments of the present invention, residue in line 118 is further separated in a second column 130, also referred to as an "acid column." Second column 130 yields a second residue in line 131 comprising acetic acid and water, and a second distillate in line 132 comprising ethanol and ethyl acetate. In one embodiment, a weight majority of the water and/or acetic acid fed to second column 130 is removed in the second residue in line 131, e.g., at least 60% of the water and/or acetic acid is removed in the second residue in line 131 or more preferably at least 80% of the water and/or acetic acid. In one embodiment, the second residue in line 131 comprise from 90% to 99.9% of the acetic acid from crude ethanol product 109, e.g., from 95% to 99.9%. An acid column may be desirable, for example, when the acetic acid concentration in the first residue is greater 50 wppm, e.g., greater than 0.1 wt. %, greater than 1 wt. %, e.g., greater than 5 wt. %. The second residue in line 131 may be fed to esterification unit 120 to convert acetic acid to one or more esters in accordance with embodiments of the present invention.

Optionally, first residue in line 118 may be preheated prior to being introduced into second column 130. The first residue in line 118 may be heat integrated with either the residue or vapor overhead of the second column 130. In some embodiments, there may be an esterification of the first residue in the vapor phase to convert some of the acetic acid and that may result in preheating a portion of first residue in line 118. For purposes of the present invention, when preheating it is preferred than less than 30 mol. % of first residue in line 118 is in the vapor phase, e.g., less than 25 mol. % or less than 20 mol. %. Greater vapor phase contents result in increased energy consumption and a significant increase in the size of second column 130. Esterifying the acetic acid in first residue in line 118 increases the ethyl acetate concentration which leads to increases in the size of second column 130 as well increases in reboiler duty. Thus, the conversion of acetic acid may be controlled depending on the initial ethyl acetate concentration withdrawn from first column. To maintain an efficient separation the ethyl acetate concentration of the first residue in line 118 feed to second column is preferably less than 1000 wppm, e.g., less than 800 wppm or less than 600 wppm.

Second column 130 operates in a manner to concentrate the ethanol from first residue so that a majority of the ethanol is carried overhead. Thus, the residue of second column 130 may have a low ethanol concentration of less than 5 wt. %, e.g. less than 1 wt. % or less than 0.5 wt. %. Lower ethanol concentrations may be achieved without significant increases in reboiler duty or column size. Thus, in some embodiments it is efficient to reduce the ethanol concentration in the residue to less than 50 wppm, or more preferably less than 25 wppm. As described herein, the residue of second column 130 may be treated and lower concentrations of ethanol allow the residue to be treated without generating further impurities.

In FIG. 1, the first residue in line 118 is introduced to second column 130 preferably in the top part of column 130, e.g., top half or top third. Feeding first residue in line 118 in a lower portion of second column 130 may unnecessarily increase the energy requirements of second column. Acid column 130 may be a tray column or packed column. In FIG. 1, second column 130 may be a tray column having from 10 to 110 theoretical trays, e.g. from 15 to 95 theoretical trays or from 20 to 75 theoretical trays. Additional trays may be used if necessary to further reduce the ethanol concentration in the residue. In one embodiment, the reboiler duty and column size may be reduced by increasing the number of trays.

Although the temperature and pressure of second column 130 may vary, when at atmospheric pressure the temperature of the second residue in line 131 preferably is from 95° C. to 160° C., e.g., from 100° C. to 150° C. or from 110° C. to 145° C. In one embodiment, when first residue in line 118 is preheated to a temperature that is within 20° C. of the temperature of second residue in line 131, e.g., within 15° C. or within 10° C. The temperature of the second distillate exiting in line 132 from second column 130 preferably is from 50° C. to 120° C., e.g., from 75° C. to 118° C. or from 80° C. to 115° C. The temperature gradient may be sharper in the base of second column 130.

The pressure of second column 130 may range from 0.1 kPa to 510 kPa, e.g., from 1 kPa to 475 kPa or from 1 kPa to 375 kPa. In one embodiment, second column 130 operates above atmospheric pressure, e.g., above 170 kPa or above 375 kPa. Second column 130 may be constructed of a material such as 316L SS, Allot 2205 or Hastelloy C, depending on the operating pressure. The reboiler duty and column size for second column remain relatively constant until the ethanol concentration in the second distillate in line 132 is greater than 90 wt. %.

As described in some embodiment, when first column 115 is operates as an extractive column with a separate water feed, the additional water is separated in second column 130. While using water as an extractive agent may reduce the reboiler duty of first column 115, when the mass flow ratio of water to organic feed is larger than 0.65:1, e.g., larger than 0.6:1 or larger than 0.54:1, the additional water will cause an increase in reboiler duty of second column 130 that offsets any benefit gained by first column 115.

Second column 130 also forms a second distillate in line 132 which may be condensed and refluxed, for example, at a ratio from 12:1 to 1:12, e.g., from 10:1 to 1:10 or from 8:1 to 1:8.

Exemplary components for the distillate and residue compositions for second column 130 are provided in Table 4 below. It should be understood that the distillate and residue may also contain other components, not listed in Table 4. For example, in optional embodiments, when ethyl acetate is in the feed to reactor 103, second residue in line 131 exemplified in Table 4 may also comprise high boiling point components.

TABLE 4

| ACID COLUMN | | | |
|---|---|---|---|
| | Conc. (wt. %) | Conc. (wt. %) | Conc. (wt. %) |
| Second Distillate | | | |
| Ethanol | 80 to 96 | 85 to 92 | 87 to 90 |
| Ethyl Acetate | <30 | 0.001 to 15 | 0.005 to 4 |
| Acetaldehyde | <20 | 0.001 to 15 | 0.005 to 4 |
| Water | <20 | 0.001 to 10 | 0.01 to 8 |
| Acetal | <2 | 0.001 to 1 | 0.005 to 0.5 |
| Second Residue | | | |
| Acetic Acid | 0.1 to 55 | 0.2 to 40 | 0.5 to 35 |
| Water | 45 to 99.9 | 55 to 99.8 | 65 to 99.5 |
| Ethyl Acetate | <0.1 | 0.0001 to 0.05 | 0.0001 to 0.01 |
| Ethanol | <5 | 0.002 to 1 | 0.005 to 0.5 |

The weight ratio of ethanol in second distillate in line 132 to ethanol in the second residue in line 131 preferably is at least 35:1. Preferably, second distillate in line 132 is substantially free of acetic acid and may contain, if any, trace amounts of acetic acid.

In one embodiment, ethyl acetate fed to second column 130 may concentrate in the second distillate in line 132. Thus, preferably no ethyl acetate is withdrawn in the second residue in line 131. Advantageously this allows most of the ethyl acetate to be subsequently recovered without having to further process the second residue in line 131.

In optional embodiments, the feed to reactor 103 may comprise acetic acid and/or ethyl acetate. When ethyl acetate is used alone as a feed, the crude ethanol product may comprise substantially no water and/or acetic acid. There may be high boiling point components, such as alcohols having more than 2 carbon atoms, e.g., n-propanol, isopropanol, n-butanol, 2-butanol, and mixtures thereof. High boiling point components refer to compounds having a boiling point that is greater than ethanol. The high boiling point components may be removed in second column 125 in the second residue in line 131 described herein.

As discussed above, according to the present invention, unreacted acetic acid in the second residue in line 131 (also referred to as the dilute acid stream) is directed to esterification unit 120. In some embodiments, the second residue in line 131 may comprise at least 85% of the acetic acid from crude ethanol product 109, e.g., at least 90% and more preferably at least 99%. In terms of ranges, the dilute acid stream optionally comprises from 85% to 99.5% or from 90% to 99.99% of the unreacted acetic acid from the crude ethanol product. In one embodiment, substantially all of the unreacted acetic acid is recovered in the second residue in line 131. By removing substantially all of the unreacted acetic acid from crude ethanol product 109, the process, in some aspects, advantageously does not require further separation of acetic acid from the ethanol. In some embodiments, the dilute acid stream comprises from 0.1 to 55 wt. % acetic acid and from 45 to about 99 wt. % water.

In one embodiment, substantially all of the unreacted acetic acid is reacted out of second residue in line 131. According to FIG. 1, second residue in line 131 is co-fed to esterification unit 120 with alcohol stream 121 to produce an ester product stream 122 comprising one or more esters and bottoms 123 comprising water. In one embodiment, ester product stream 122 and/or bottoms 123 may be substantially free of acetic acid. Second residue in line 131 may be fed to esterification unit 120 at a temperature from 20 to 90° C., e.g., from 25 to 75° C. Preheating may be used as necessary. In some embodiments, alcohol stream 121 and second residue in line 131 are fed to the esterification unit in a counter-current manner to facilitate the production of a reaction product. In another embodiment, not shown, alcohol stream 121 may be added directly to second residue in line 131 prior to being introduced into esterification unit 120.

In some embodiments, esterification unit 120 comprises a reaction zone comprising a reactor, coupled to a separation zone comprising one or more distillation columns and/or stripping columns. Suitable reactors for use in the esterification include batch reactors, continuously-fed stirred-tank reactors, plug-flow reactors, reactive distillation towers, or a combination thereof. In some embodiments, an acid catalyst is fed to the reactor to facilitate the esterification of the acetic acid. Suitable acid catalysts for use in the present invention include, but are not limited to sulfuric acid, phosphoric acid, sulfonic acids, heteropolyacids, other mineral acids and a combination thereof.

The residence time of esterification unit 120 may impact acetic acid conversion. In some embodiments, for example, the residence time in esterification unit 120 is from 0.1 to 5 hours, e.g., from 0.2 to 3 hours, or less than 1 hour.

The distillation column for the esterification unit 120 may comprise from 5 to 70 theoretical trays, e.g., from 10 to 50 theoretical trays or from 15 to 30 theoretical trays. The reflux of ester product stream 122 may be from 10:1 to 1:10, e.g., from 5:1 to 1:5 or from 2:1 to 1:2.

The operating parameters of esterification unit 120 may be varied to achieve a desired composition in ester product stream 122. For example, in some embodiments, temperature, pressure, feed rates, and residence times can be varied to increase conversion of acetic acid to an ester, decrease the formation of impurities, achieve more efficient separation, reduce energy consumption, or combinations thereof.

In one embodiment, esterification unit 120 operates at a base temperature from 100° C. to 150° C., e.g., from 100° C. to 130° C., or from 100° C. to 120° C. In terms of pressure, esterification unit 120 may be operated at atmospheric pressure, subatmospheric pressure, or superatmospheric pressure. For example, in some embodiments, esterification unit 120 operates at a pressure from 50 kPa to 500 kPa, e.g., from 50 kPa to 400 kPa, or from 50 kPa to 200 kPa.

In some embodiments, the feed rates of acetic acid and alcohol to the esterification unit 120 may be adjusted to control the molar ratio of acetic acid to alcohol being fed to the esterification unit 120. For example, in some embodiments, the molar ratio of acetic acid to methanol fed to the esterification unit 120 is from 1:1 to 1:50, e.g., from 1:2 to 1:35, or from 1:5 to 1:20.

The processes of the present invention preferably provide for a high conversion of acetic acid to ester(s). In one embodiment, at least 60%, e.g., at least 75%, at least 90% or at least 95% of the acetic acid in the second residue in line 131 is converted to an ester. Lower conversion of acetic acid may be tolerated if the acetic acid concentration in second residue in line 132 is relatively low.

The ester product stream 122 exiting the esterification unit 120 preferably comprises at least one ester. Exemplary compositions when using methanol as the alcohol stream 121 from the esterification unit 120 are provided in Table 5, below. It should also be understood that these compositions may also contain other components, not listed in Table 5. Lower amounts of the ester may be possible when higher concentrations of the alcohols are fed to the reactor relative to the acetic acid to be reacted. When excess alcohol is reacted with the acetic acid from the second residue in line 131, some alcohol also may be present in the ester product stream 122.

TABLE 5

ESTERIFICATION UNIT 120

|  | Conc. (wt. %) | Conc. (wt. %) | Conc. (wt. %) |
|---|---|---|---|
| Ester Product Stream |  |  |  |
| Methyl Acetate | 1 to 90 | 5 to 85 | to 90 |
| Methanol | 40 to 99.9 | 45 to 95 | 50 to 90 |
| Water | <1 | 0.001 to 0.5 | 0.001 to 0.1 |
| Acetic Acid | <0.1 | <0.5 | nd |
| Ether | <1 | 0.001 to 0.5 | 0.001 to 0.1 |
| Bottoms |  |  |  |
| Water | 90 to 99.9 | 92 to 99.9 | 95 to 99.9 |
| Acetic Acid | <5 | 0.001 to 3 | 0.01 to 1 |
| Methanol | <1 | <0.001 | nd |
| Methyl Acetate | <1 | <0.05 | 0.0001 to 0.005 |

Some impurities, such as dimethyl ether may form over the course of the reaction in esterification unit 120. These impurities may be present in very low amounts, or even no detectable amounts, in the ester product stream 122. In some embodiments, the ester product stream 122 comprises less than 1000 wppm dimethyl ether, e.g., less than 750 wppm, or less than 500 wppm.

In some embodiments, esterification unit 120 comprises a reactive distillation column. Reactive distillation column comprises an ion exchange resin bed, an acidic catalyst, or combinations thereof. Non-limiting examples of ion exchange resins suitable for use in the present invention include macroporous strong-acid cation exchange resins such as those from the Amberlyst® series distributed by Rohm and Haas. Additional ion exchange resins suitable for use in the present invention are disclosed in U.S. Pat. Nos. 4,615,806, 5,139,981, and 7,588,690, the disclosures of which are incorporated by reference in their entireties. In other embodiments, reactive distillation column comprises an acid selected from the group consisting of sulfuric acid, phosphoric acid, sulfonic acids, heteropolyacids, other mineral acids and a combination thereof. In other embodiments, acid catalysts include zeolites and supports treated with mineral acids and heteropolyacids. When an acid catalyst is used, e.g., sulfuric acid, the acid catalyst is fed to the reactive distillation column.

In some embodiments, second residue in line 131 is optionally fed to a guard bed (not shown) and then fed to esterification unit 120. In this aspect, the guard bed comprises an ion exchange resin, such as those disclosed above. While not being bound to any particular theory, the guard bed removes one or more corrosive metals present in the second residue in line 131, thereby minimizing the deactivation of any ion exchange resin catalytic sites in the ion exchange resin present in esterification unit 120.

Bottoms 123 comprising water and may be substantially free of acetic acid. In one embodiment, a portion of bottoms 123 in line 124 may be directed to first column 115 as an optional extractive agent. In other embodiments bottoms 123 may be used to hydrolysis a stream comprises ethyl acetate or diethyl acetal. Bottoms 123 may also be neutralized and/or diluted before being disposed of to a waste water treatment facility. The organic content, e.g., acetic acid content, of bottoms 123 beneficially may be suitable to feed microorganisms used in a waste water treatment facility.

Figure 2:
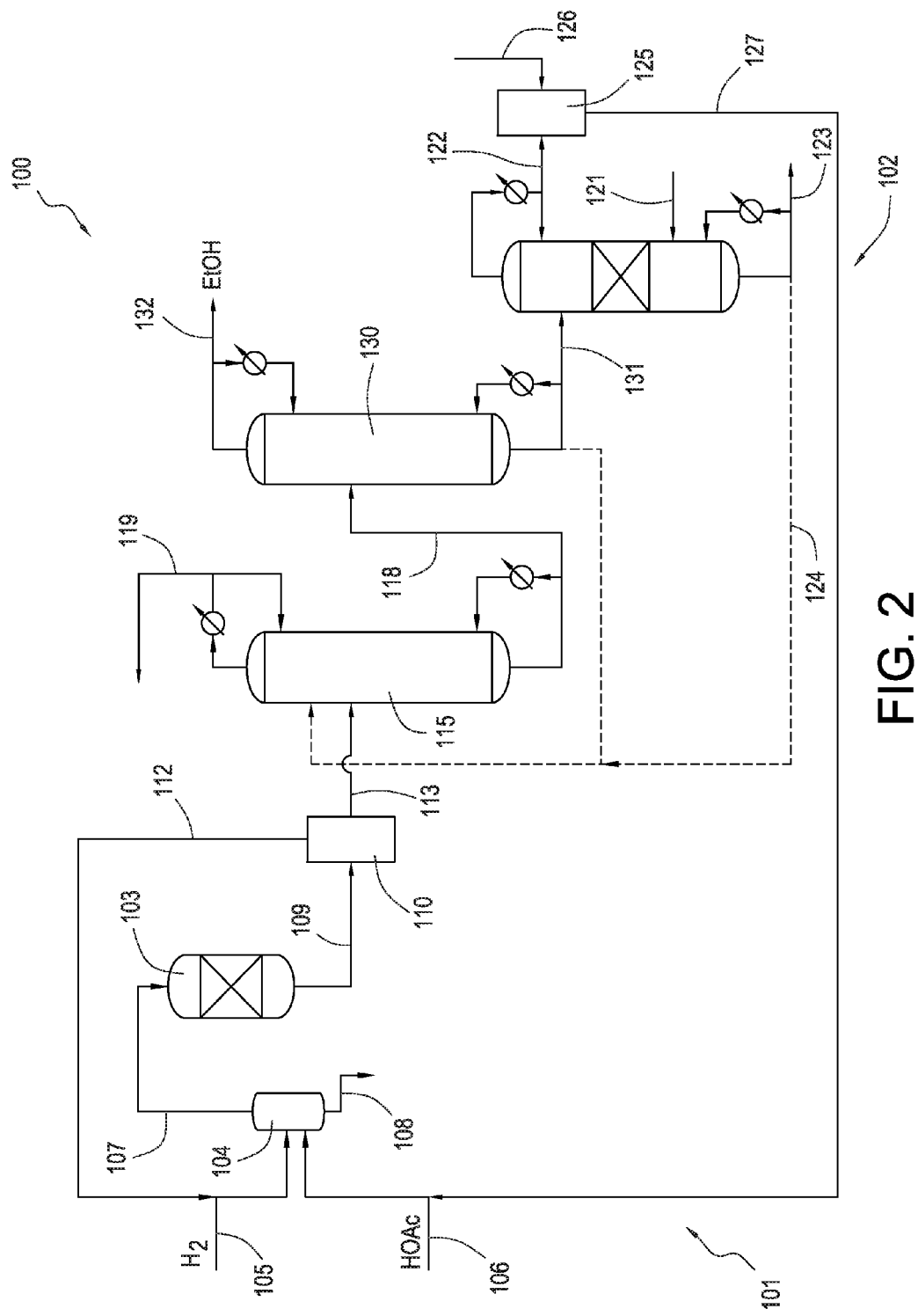
FIG. 2 is a schematic diagram of an integrated hydrogenation and carbonylation process in accordance with one embodiment of the present invention.

As described above, ester product stream 122 may be further processed and/or refined. As shown in FIG. 2, ester product stream 122 is fed to carbonylation process 125 along with carbon monoxide 126, wherein process 122 results in a product stream 127 comprising acetic acid. Suitable carbonylation processes are described above. This allows an indirect recycle of the unreacted acetic acid in the hydrogenation process through the carbonylation process and back to the hydrogenation process.

In an optional embodiment, ester product stream may be reduced with hydrogen to form ethanol via hydrogenolysis. The resulting ethanol may be removed as a separate product or recycled to the process, such as to first column 115, second column 130, or esterification unit 120.

In one embodiment, as shown in FIG. 3, due to the presence of ethyl acetate in second distillate in line 132, an additional third column 140 may be used. A third column 140, referred to as a "product" column, is used for removing ethyl acetate from second distillate in line 132 and producing an ethanol product in the third residue in line 141. Product column 140 may be a tray column or packed column. In FIG. 3, third column 140 may be a tray column having from 5 to 90 theoretical trays, e.g. from 10 to 60 theoretical trays or from 15 to 50 theoretical trays.

The feed location of second distillate in line 132 may vary depending on ethyl acetate concentration and it is preferred to feed second distillate in line 132 to the upper portion of third column 140. Higher concentrations of ethyl acetate may be fed at a higher location in third column 140. The feed location should avoid the very top trays, near the reflux, to avoid excess reboiler duty requirements for the column and an increase in column size. For example, in a column having 45 actual trays, the feed location should between 10 to 15 trays from the top. Feeding at a point above this may increase the reboiler duty and size of third column 140.

Second distillate in line 132 may be fed to third column 140 at a temperature of up to 70° C., e.g., up to 50° C., or up to 40° C. In some embodiments it is not necessary to further preheat second distillate in line 132.

Ethyl acetate may be concentrated in the third distillate in line 142. Due to the relatively lower amounts of ethyl acetate fed to third column 140, third distillate in line 142 also comprises substantial amounts of ethanol. To recover the ethanol, third distillate in line 142 may be fed to first column as an ethyl acetate recycle stream 117. Depending on the ethyl acetate concentration of ethyl acetate recycle stream 117 this stream may be introduced above or near the feed point of the liquid stream 113. Depending on the targeted ethyl acetate concentration in the distillate of first column 115 the feed point of ethyl acetate recycle stream 117 will vary. Liquid stream 113 and ethyl acetate recycle stream 117 collectively comprise the organic feed to first column 115. In one embodiment, organic feed comprises from 1 to 25% of ethyl acetate recycle stream 117, e.g., from 3% to 20% or from 5% to 15%. This amount may vary depending on the production of reactor 103 and amount of ethyl acetate to be recycled.

Because ethyl acetate recycle stream 117 increases the demands on the first and second columns, it is preferred that the ethanol concentration in third distillate in line 142 be from 70 to 90 wt. %, e.g., from 72 to 88 wt. %, or from 75 to 85 wt. %. In other embodiments, a portion of third distillate in line 142 may be purged from the system in line 143 as additional products, such as an ethyl acetate solvent. In addition, ethanol may be recovered from a portion of the third distillate in line 142 using an extractant, such as benzene, propylene glycol, and cyclohexane, so that the raffinate comprises less ethanol to recycle.

In an optional embodiment, the third residue may be further processed to recover ethanol with a desired amount of water, for example, using a further distillation column, adsorption unit, membrane or combination thereof, may be used to further remove water from third residue in line 141 as necessary.

Third column 140 is preferably a tray column as described above and preferably operates at atmospheric pressure. The temperature of the third residue in line 141 exiting from third column 140 preferably is from 65° C. to 110° C., e.g., from 70° C. to 100° C. or from 75° C. to 80° C. The temperature of the third distillate in line 142 exiting from third column 140 preferably is from 30° C. to 70° C., e.g., from 40° C. to 65° C. or from 50° C. to 65° C.

The pressure of third column 140 may range from 0.1 kPa to 510 kPa, e.g., from 1 kPa to 475 kPa or from 1 kPa to 375 kPa. In some embodiments, third column 140 may operate under a vacuum of less than 70 kPa, e.g., less than 50 kPa, or less than 20 kPa. Decreases in operating pressure substantially decreases column diameter and reboiler duty for third column 140.

Exemplary components for ethanol mixture stream and residue compositions for third column 140 are provided in Table 6 below. It should be understood that the distillate and residue may also contain other components, not listed in Table 6.

TABLE 6

PRODUCT COLUMN

|  | Conc. (wt. %) | Conc. (wt. %) | Conc. (wt. %) |
|---|---|---|---|
| Third Distillate |  |  |  |
| Ethanol | 70 to 99 | 72 to 95 | 75 to 90 |
| Ethyl Acetate | 1 to 30 | 1 to 25 | 1 to 15 |
| Acetaldehyde | <15 | 0.001 to 10 | 0.1 to 5 |
| Water | <10 | 0.001 to 2 | 0.01 to 1 |
| Acetal | <2 | 0.001 to 1 | 0.01 to 0.5 |
| Third Residue |  |  |  |
| Ethanol | 80 to 99.5 | 85 to 97 | 90 to 95 |
| Water | <3 | 0.001 to 2 | 0.01 to 1 |
| Ethyl Acetate | <1.5 | 0.0001 to 1 | 0.001 to 0.5 |
| Acetic Acid | <0.5 | <0.01 | 0.0001 to 0.01 |

Figure 4:
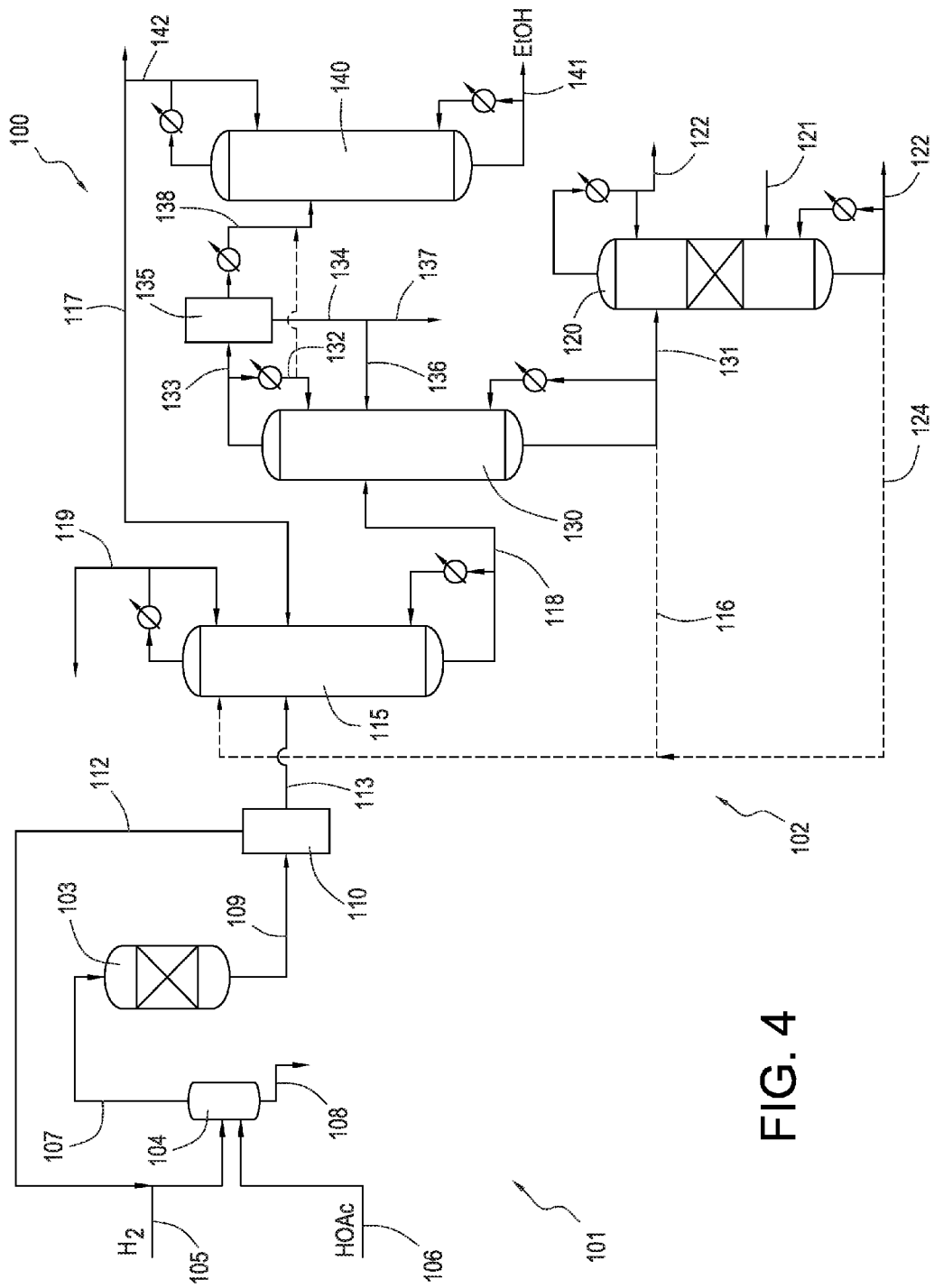
FIG. 4 is a schematic diagram of an acetic acid reduction system for an ethanol production process to reduce water concentrations prior to the product column in accordance with one embodiment of the present invention.

In another embodiment, water may be removed prior to recovering the ethanol product. As shown in FIG. 4, second column 130 also forms an overhead, which is withdrawn in line 133. The overhead in line 133 preferably comprises 85 to 92 wt. % ethanol, e.g., about 87 to 90 wt. % ethanol, with the remaining balance being water and ethyl acetate. In one embodiment, the overhead in line 133 may comprise less than 15 wt. % water, e.g., less than 10 wt. % water or less than 8 wt. % water. As shown in FIG. 4, overhead vapor in line 133 may be fed to water separator 135, which may be an adsorption unit, membrane, molecular sieves, light ends column distillation, or a combination thereof. In one embodiment, at least 50% of overhead vapor is fed to water separator 135, e.g., at least 75% or at least 90%. Optionally, some of overhead vapor in line 133 is condensed as second distillate 132 and optionally may be fed directly to third distillation column 140.

Water separator 135 in FIG. 4 may be a pressure swing adsorption (PSA) unit. For purposes of clarity the details of the PSA unit are not shown in the figures. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 135 may remove at least 95% of the water overhead vapor 133, and more preferably from 95% to 99.99% of the water from vapor overhead 133, into a water stream 134. All or a portion of water stream 134 may be returned to second column 130 in line 136, which may increase the reboiler duty and/or size of second column 130. Additionally or alternatively, all or a portion of water stream may be purged via line 137. The remaining portion of vapor overhead 133 exits the water separator 135 as ethanol mixture stream 138. In one embodiment, ethanol mixture stream 138 comprises more than 92 wt. % ethanol, e.g., more than 95 wt. % or more than 99 wt. %. In one embodiment a portion of water stream 137 may be fed to first column 115 as the extractive agent.

A portion of vapor overhead 133 may be condensed and refluxed to second column 130, as shown, for example, at a ratio from 12:1 to 1:12, e.g., from 10:1 to 1:10 or from 8:1 to 1:8. The second distillate in line 132 optionally may be mixed with ethanol mixture stream 138 and co-fed to product column 140. This may be necessary if additional water is needed to improve separation in product column 140. It is understood that reflux ratios may vary with the number of stages, feed locations, column efficiency and/or feed composition. Operating with a reflux ratio of greater than 3:1 may be less preferred because more energy may be required to operate second column 130.

The ethanol product produced by the process of the present invention may be an industrial grade ethanol or fuel grade ethanol. Exemplary finished ethanol compositional ranges are provided below in Table 7.

TABLE 7

| FINISHED ETHANOL COMPOSITIONS | | | |
|---|---|---|---|
| Component | Conc. (wt. %) | Conc. (wt. %) | Conc. (wt. %) |
| Ethanol | 85 to 99.9 | 90 to 99.5 | 92 to 99.5 |
| Water | <12 | 0.1 to 9 | 0.5 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

The finished ethanol composition produced by the embodiments of the present invention may be used in a variety of applications including applications as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene.

In order that the invention disclosed herein may be more efficiently understood, an example is provided below. It should be understood that this example is for illustrative purposes only and is not to be construed as limiting the invention in any manner.

EXAMPLES

Example 1

A reactive distillation column having a 2 inch diameter reactive distillation section between an absorbing section and a stripping section was used to react the acetic acid. A 20 wt. % acetic acid solution in water was fed into the reactive distillation column on the top of the reactive zone at 0.11 g/min. A pure methanol solution was fed into the same column at the bottom of the reactive zone at 0.38 g/min. The reflux-to-distillate flow rate ratio in this experiment was 2.0. The composition of the distillate was 59.4 wt. % methanol, 40.1 wt. % methyl acetate, 0.5 wt. % water, and less than 0.01 wt. % acetic acid. The composition of the bottoms was 99 wt. % water, 1 wt. % acetic acid, 11 wppm methyl acetate and less than 0.01 wt. % methanol.

Example 2

A column containing Amberlyst 36®, a macroporous sulfonic acid resin catalyst from Rohm and Hass (now a part of Dow). The column consisted of three sections: i) a bottom stripping section, 1.0 in ID, containing 15 Oldershaw trays; ii) a reactive section, 2.0 in ID and 2-ft long, containing the catalyst in structured packing elements; and iii) an upper rectification section, 1.0 in ID, containing 10 Oldershaw trays. All sections were vacuum jacket.

An aqueous stream containing 20 wt. % acetic acid was fed at the top of the reactive section, whereas a methanol stream (99.7 wt. % methanol) was fed directly below the reactive section. Each feed line is provided with a heating tape for temperature control. All temperatures are read using type-K thermocouples. All flow rates are measured using low flow Coriolis meters. Organic compounds are analyzed by gas chromatographic, using two different calibration ranges. Water is determined by Karl-Fisher titration.

The aqueous acetic acid stream was fed at a temperature of 69.7° C. and a flow rate of 2 g/min. The methanol stream was fed at a temperature of 39.1° C. and a flow rate of 0.92 g/min. The column was operated at atmospheric pressure. The top temperature was 60.4° C. and the bottom temperature was 100.2° C. The distillate from the column was refluxed at an R/D ratio of 1.45. The reactive distillation achieved 94% acetic acid conversion into methyl acetate. The composition of the distillate was 60.5 wt. % methanol, 39.3 wt. % methyl acetate, 0.2 wt. % water, and less than 0.01 wt. % acetic acid. The composition of the bottoms was 98.9 wt. % water, 1.14 wt. % acetic acid, 44 wppm methyl acetate and 48 wppm methanol.

Example 3

Using the same column as Example 2, an dilute acid stream comprising 4.1 wt. % acetic acid was fed at a temperature of 75.7° C. and a flow rate of 4.76 g/min. The methanol stream was fed at a temperature of 40.4° C. and a flow rate of 1.08 g/min. The column was operated at atmospheric pressure. The top temperature was 67° C. and the bottom temperature was 100.3° C. The distillate from the column was refluxed at an R/D ratio of 1.53. The reactive distillation achieved 77% acetic acid conversion into methyl acetate. The composition of the distillate was 81.9 wt. % methanol, 13.9 wt. % methyl acetate, 4.2 wt. % water, and less than 0.01 wt. % acetic acid. The composition of the bottoms was 99.3 wt. % water, 0.67 wt. % acetic acid, 2 wppm methyl acetate and 31 wppm methanol.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising:
   hydrogenating acetic acid and/or an ester thereof in a reactor in the presence of a catalyst to form a crude ethanol product;
   separating a portion of the crude ethanol product in a first distillation column to yield a first distillate comprising acetaldehyde and ethyl acetate, and a first residue comprising ethanol, acetic acid, and water;
   separating a portion of the first residue in a second distillation column to yield a second residue comprising acetic acid and water and a second distillate comprising ethanol;
   reacting the acetic acid from a first portion of the second residue with at least one alcohol in an esterification unit to produce at least one ester product stream, and a water stream that is substantially free of acetic acid; and
   recovering ethanol from the second distillate.

2. The process of claim 1, wherein the water stream comprises less than 1 wt. % acetic acid.

3. The process of claim 1, wherein the second residue comprises from 90% to 99.9% of the acetic acid in the crude ethanol product.

4. The process of claim 1, wherein the conversion of acetic acid in the hydrogenating step is greater than 60%.

5. The process of claim 1, wherein the second residue comprises less than 1 wt. % ethanol and/or ethyl acetate.

6. The process of claim 1, wherein the conversion of acetic acid in the esterification step is greater than 60%.

7. The process of claim 1, wherein the at least one alcohol is selected from the group consisting of methanol, ethanol, propanol, butanol, pentanol, and isomers and mixtures thereof.

8. The process of claim 1, wherein the at least one ester is selected from the group consisting of methyl acetate, ethyl acetate, propyl acetate, butyl acetate, pentyl acetate, and isomers and mixtures thereof.

9. The process of claim 1, wherein the ester product stream comprises one or more esters and the at least one alcohol fed to the esterification unit, provided the ester product stream is substantially free of acetic acid.

10. The process of claim 1, wherein the second residue stream and the at least one alcohol are fed to the esterification unit at a molar ratio of acetic acid to alcohol from 1:1 to 1:50.

11. The process of claim 1, wherein the esterification unit comprises a strongly acidic ion exchange resin bed.

12. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

13. The process of claim 1, wherein the ester product stream is reacted with carbon monoxide to form acetic acid that is directed to the hydrogenation reactor.

14. The process of claim 1, further comprising directing a second portion of the second residue to the first column as an extractive agent.

15. The process of claim 1, further comprising directing a portion of the water stream to the first column as an extractive agent.

16. The process of claim 1, wherein the first residue and the second distillate comprise ethyl acetate, and further comprising separating the second distillate in a third distillation column to yield a third distillate comprising ethyl acetate and third residue comprising ethanol.

17. The process of claim 16, wherein the third distillate is directed to the first column.

18. The process of claim 16, wherein the second distillate comprises water, and further comprising removing the water prior to the third column.

19. A process for producing ethanol, comprising:
hydrogenating acetic acid and/or an ester thereof in a reactor in the presence of a catalyst to form a crude ethanol product;
separating a portion of the crude ethanol product in a first distillation column to yield a first distillate comprising acetaldehyde and ethyl acetate, and a first residue comprising ethanol, acetic acid, and water;
separating a portion of the first residue in a second distillation column to yield a second residue comprising acetic acid and water and a second distillate comprising ethanol;
reacting the acetic acid from a first portion of the second residue with methanol in an esterification unit to produce at least one ester product stream comprising methanol, methyl acetate, and a water stream, provided that the at least one ester product stream and water stream are substantially free of acetic acid; and
recovering ethanol from the second distillate.

20. A process for producing ethanol, comprising:
hydrogenating acetic acid and/or an ester thereof in a reactor in the presence of a catalyst to form a crude ethanol product;
separating a portion of the crude ethanol product in a first distillation column to yield a first distillate comprising acetaldehyde and ethyl acetate, and a first residue comprising ethanol, acetic acid, and water;
separating a portion of the first residue in a second distillation column to yield a second residue comprising acetic acid and water and a second distillate comprising ethanol and ethyl acetate;
reacting the acetic acid from a first portion of the second residue with at least one alcohol in an esterification unit to produce at least one ester product stream, and a water stream that is substantially free of acetic acid; and
separating a portion of the second distillate in a third distillation column to yield a third distillate comprising ethyl acetate and third residue comprising ethanol.

* * * * *